(12) United States Patent
Linz et al.

(10) Patent No.: US 8,466,318 B2
(45) Date of Patent: Jun. 18, 2013

(54) METHOD OF PREPARING CHIRAL CYCLIC β-AMINOCARBOXAMIDES

(75) Inventors: Guenter Linz, Mittelbiberach (DE); Gerd Kraemer, Eberhardzell (DE); Zeno A. Leuter, Weingarten (DE); Markus Ostermeier, Biberach (DE); Werner Rall, Mittelbiberach (DE); Claudia Ochs, Ehingen (DE); Rolf Schmid, Baltringen (DE)

(73) Assignee: Boehringer Ingelheim International GmbH (DE)

( * ) Notice: Subject to any disclaimer, the term of this patent is extended or adjusted under 35 U.S.C. 154(b) by 758 days.

(21) Appl. No.: 12/301,131

(22) PCT Filed: May 15, 2007

(86) PCT No.: PCT/EP2007/054728
§ 371 (c)(1),
(2), (4) Date: Feb. 26, 2009

(87) PCT Pub. No.: WO2007/135036
PCT Pub. Date: Nov. 29, 2007

(65) Prior Publication Data
US 2009/0209787 A1 Aug. 20, 2009

(30) Foreign Application Priority Data

May 18, 2006 (EP) .................................. 06114182

(51) Int. Cl.
C07C 233/00 (2006.01)
C07C 235/00 (2006.01)
C07C 237/00 (2006.01)
C07C 239/00 (2006.01)

(52) U.S. Cl.
USPC ............ 564/164; 564/163; 564/189; 564/191

(58) Field of Classification Search
None
See application file for complete search history.

(56) References Cited

U.S. PATENT DOCUMENTS 6,835,841 B2 * 12/2004 Deerberg et al. ............. 546/244
7,468,459 B2 * 12/2008 Xiao et al. .................... 564/336
2004/0082795 A1    4/2004 Deerberg et al.

FOREIGN PATENT DOCUMENTS

WO    2004/085378 A1    10/2004
WO    2005054178 A1    6/2005

OTHER PUBLICATIONS

Ghattas et al., "Enamine chemistry. XXVII. Reduction of enaminones, enaminothiones and thioamides by LiAlH4 and NaBH4," Acta Chemica Scandinavica B, (1982) 36: 505-511.*

Johnson, D., "The synthesis of N-alkyl-2-oxocyclopentane-carboxyamides," J.Chem.Soc. (1958) 1624-8.*
Rohloff, J. et al. "Practical total synthesis of RS-15385," J.Org.Chem. (1993) 58: 1935-1938.*
Sibi, M., et al. "Chemoselective Dieckmann-like condensations using N-methoxy-N-methaylamides," Tet. Lett. (1995) 36: 6209-6212.*
Ohkura, H. et al. "Chemo- and regioselectivity in the reactions between highly electrophilic fluorine containing dicarbonyl compounds and amines. Improved synthesis of the corresponding imines/enamines," Tetrahedron (2003) 59: 1647-56.*
David, O. et al. "Enamino ester reduction: A short enantioselective route to pyrrolizidine and indolizidine alkaloids. Synthesis of (+)-laburnine, (+)-tashiromine, and (−)-isoretronecanol," J.Org.Chem. (1999) 64: 3122-31.*
Blot, J. et al. "Chiral cyclic β—amino esters. Part II: Synthesis by diasteroselective reduction of enamino esters," Tetrahedron Lett. (1997) 38: 8511-14.*
Calvet, S. et al. "Chiral heterocyclic β—enamino esters: convenient synthesis and diastereoselective reduction," Tetrahedron (2003) 39: 6333-39.*
Haviari, G. et al. "Asymmetric synthesis with chiral hydrogenolysable amines. Cyclic β-enamino ester reduction. A diastereoselective route to 2,3-disubstituted pyrrolidines," Tetrahedron Lett. (1992) 33: 4311-2.*

(Continued)

*Primary Examiner* — Porfirio Nazario Gonzalez
*Assistant Examiner* — James Meadows
(74) *Attorney, Agent, or Firm* — Michael P. Morris; Mary-Ellen M. Devlin

(57) ABSTRACT

The present invention encompasses a process for preparing compounds of formula (1),

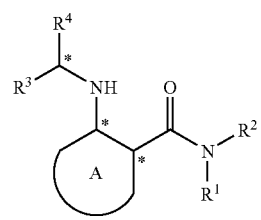

(1)

wherein a compound of formula (2)

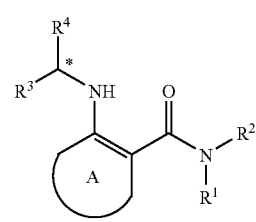

(2)

is reacted in the presence of a catalyst and a solvent under hydrogen pressure to form a compound of formula (1) and wherein A and $R^1$—$R^4$ are defined herein.

6 Claims, No Drawings

OTHER PUBLICATIONS

Bartoli, G. et al. "Chemo- and diastereoselective reduction of β-enamino esters: A convenient synthesis of both cis- and trans-γ-amino alcohols and β-amino esters," J.Org.Chem. (1994) 59: 5328-35.*

Desmaele, D. et al., "Stereocontrolled elaboration of quaternary carbon centers through the asymmetric Michael-type alkylation of chiral iminies/secondary enamines: enantioselective synthesis of (+)-vincamine," J.Org.Chem. (1997) 62: 3890-3901.*

P. Audebert, et al; Electrochemical Evidence for Intramolecular Reactions of the Electrogenerated Cation—Radicals of Some Amidoenamines; Journal of Electroanalytical Chemistry (1995) vol. 389 pp. 215-218.

Daniel Nöteberg, et al; Systhesis of Enantiomerically Pure cis and trans 2-Aminocyclopentanecarboxylic Acids. Use of Proline Replacements in Potential HIV-Protease Inhibitors; Tetrahedron (1997) vol. 53, No. 23 pp. 7975-7984.

International Search Report for PCT/EP2007/054728 mailed Jul. 19, 2007.

* cited by examiner

METHOD OF PREPARING CHIRAL CYCLIC β-AMINOCARBOXAMIDES

This application is a national phase entry under 35 U.S.C. 371 of international application PCT/EP2007/054728, filed May 15, 2007, which claims priority to European Application No. EP 06114182.6, filed May 18, 2006, each of which is hereby incorporated by reference in its entirety.

The invention relates to a new method of preparing chiral cyclic β-aminocarboxamides. β-Aminocarboxamides are synthesis components which are of value in organic synthesis for building peptidomimetic structures.

BACKGROUND TO THE INVENTION

A method of preparing the salts of chiral, substituted cyclic β-aminoesters is described in U.S. Pat. No. 6,835,841. In this method, a cyclic β-enaminoester which is formally obtainable by reacting a cyclic β-ketoester with an amine is hydrogenated in the presence of a platinum catalyst under hydrogen pressure, while an acid, for example acetic acid, is added in an excess in relation to the hydrogenation substrate. The method described cannot readily be applied to the synthesis of chiral cyclic β-aminocarboxamides, particularly if the nitrogen of the enamine is substituted by a 1-phenylethyl group, for example. In this case, under the known conditions, hydrogenation of the aromatic ring also occurs, with the result that the hydrogenolytic cleaving of the chiral auxiliary to form the free β-aminocarboxamides becomes impossible.

The aim of the present invention is to provide a method for the direct preparation of cyclic β-aminocarboxamides with a high diastereoselectivity and yield.

DETAILED DESCRIPTION OF THE INVENTION

This aim is achieved by the process according to the invention for preparing compounds of formula (1),

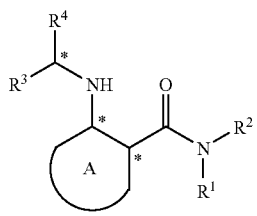

(1)

wherein
A denotes $C_{4-10}$cycloalkyl or 5-10 membered heterocycloalkyl, the latter containing a heteroatom or a group of heteroatoms, selected from among —O—, —$NR^c$— and —$S(O)_n$—, and
$R^1$ and $R^2$ each independently denote hydrogen or a group selected from among $C_{1-8}$alkyl, $C_{3-8}$cycloalkyl, $C_{4-12}$cycloalkylalkyl, 5-6 membered heteroaryl and 3-8 membered heterocycloalkyl, optionally substituted by one or more identical or different $R^a$ and/or $R^b$, or
$R^1$ and $R^2$ together with the nitrogen atom to which they are bound form a 3-14 membered heterocycloalkyl or 5-12 membered heteroaryl, this ring system optionally being substituted by one or more identical or different $R^a$ and/or $R^b$, and
$R^3$ denotes $C_{6-10}$aryl or 5-12 membered heteroaryl, optionally substituted by one or more identical or different $R^a$ and/or $R^b$, and
$R^4$ denotes hydrogen or a $C_{1-6}$alkyl optionally substituted by one or more identical or different $R^a$ and/or $R^b$, or
$R^3$ and $R^4$ together with the carbon atom to which they are bound form a $C_{3-10}$cycloalkyl or 3-14 membered heterocycloalkyl, while this ring may optionally be fused to an aryl or heteroaryl and the resulting ring system may optionally be substituted by one or more identical or different $R^a$ and/or $R^b$, and
n denotes 0, 1 or 2, and
each $R^a$ is independently selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-8 membered heterocycloalkyl and 4-14 membered heterocycloalkylalkyl, and
each $R^b$ denotes a suitable group and is independently selected from among —$OR^c$, $C_{1-3}$-haloalkyloxy, —$OCF_3$, —$SR^c$, —$NR^cR^c$, —$ONR^cR^c$, —$N(OR^c)R^c$, —$N(R^c)NR^cR^c$, halogen, —$CF_3$, —CN, —NC, —OCN, —SCN, —NO, —$NO_2$, —$N_3$, —$S(O)R^c$, —$S(O)OR^c$, —$S(O)_2R^c$, —$S(O)_2OR^c$, —$S(O)NR^cR^c$, —$S(O)_2NR^cR^c$, —$OS(O)R^c$, —$OS(O)_2R^c$, —$OS(O)_2OR^c$, —$OS(O)NR^cR^c$, —$OS(O)_2NR^cR^c$, —$C(O)R^c$, —$C(O)OR^c$, —$C(O)SR^c$, —$C(O)NR^cR^c$, —$C(O)N(R^c)NR^cR^c$, —$C(O)N(R^c)OR^c$, —$C(NR^c)NR^cR^c$, —$C(NOH)R^c$, —$C(NOH)NR^cR^c$, —$OC(O)R^c$, —$OC(O)OR^c$, —$OC(O)SR^c$, —$OC(O)NR^cR^c$, —$OC(NR^c)NR^cR^c$, —$SC(O)R^c$, —$SC(O)OR^c$, —$SC(O)NR^cR^c$, —$SC(NR^c)NR^cR^c$, —$N(R^c)C(O)R^c$, —$N[C(O)R^c]_2$, —$N(OR^c)C(O)R^c$, —$N(R^c)C(NR^c)R^c$, —$N(R^c)N(R^c)C(O)R^c$, —$N[C(O)R^c]NR^cR^c$, —$N(R^c)C(S)R^c$, —$N(R^c)S(O)R^c$, —$N(R^c)S(O)OR^c$, —$N(R^c)S(O)_2R^c$, —$N[S(O)_2R^c]_2$, —$N(R^c)S(O)_2OR^c$, —$N(R^c)S(O)_2NR^cR^c$, —$N(R^c)[S(O)_2]_2R^c$, —$N(R^cC(O)OR^c$, $N(R^c)C(O)SR^c$, —$N(R^c)C(O)NR^cR^c$, —$N(R^c)C(O)NR^cNR^cR^c$, —$N(R^c)N(R^c)C(O)NR^cR^c$, —$N(R^c)C(S)NR^cR^c$, —[$N(R^c)C(O)]_2R^c$, —$N(R^c)[C(O)]_2R^c$, —$N\{[C(O)]_2R^c\}_2$, —$N(R^c)[C(O)]_2OR^c$, —$N(R^c)[C(O)]_2NR^cR^c$, —$N\{[C(O)]_2OR^c\}_2$, —$N\{[C(O)]_2NR^cR^c\}_2$, —[$N(R^c)C(O)]_2OR^c$, —$N(R^c)C(NR^c)OR^c$, —$N(R^c)C(NOH)R^c$, —$N(R^c)C(NR^c)SR^c$ and —$N(R^c)C(NR^c)NR^cR^c$, and
each $R^c$ independently denotes hydrogen or $C_{1-6}$alkyl, while a compound of general formula (2)

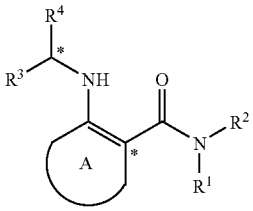

(2)

is hydrogenated in the presence of a catalyst and a solvent under hydrogen pressure to form a compound of general formula (1).

In one aspect of the invention the method described above is characterised in that the hydrogenation is carried out without any addition of acids.

In another aspect the invention relates to the method described herein before wherein A denotes $C_{4-7}$cycloalkyl.

In another aspect the invention relates to a method wherein a compound of general formula (2a)

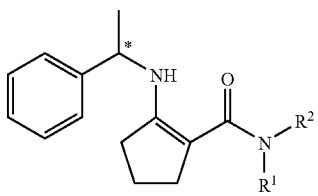

(2a)

is hydrogenated in the presence of a catalyst and a solvent under hydrogen pressure to form a compound of general formula (1a)

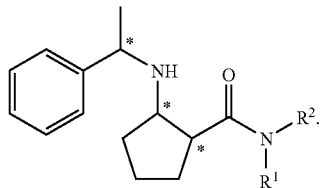

(1a)

In another aspect the invention relates to the method described herein before wherein platinum(IV)-dioxide is used as catalyst.

In another aspect the invention relates to a method wherein a compound of general formula (3)

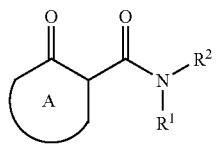

(3)

is reacted with a primary amine of general formula (4)

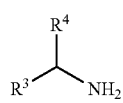

(4)

in the presence of a dehydrating agent or solvent to form a compound of general formula (2).

In another aspect the invention relates to a method as described herein before wherein a compound of general formula (5)

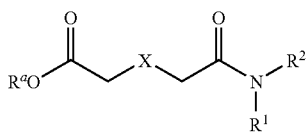

(5)

is intramolecularly cyclised under basic conditions in the presence of a solvent to form a compound of general formula (3), wherein X denotes a 1-7 membered alkylene bridge in which a methylene group may be replaced by a heteroatom or a group of heteroatoms selected from among —O—, —NR$^c$— and —S(O)$_n$—.

In another aspect the invention relates to a method wherein a compound of general formula (1) is reacted in the presence of palladium or palladium(II)-hydroxide on charcoal and a solvent under hydrogen pressure to form a compound of general formula (6)

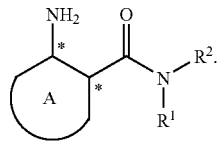

(6)

In another aspect the invention relates to a method wherein a compound of general formula (3a)

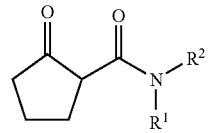

(3a)

is reacted with 1-phenylethylamine in the presence of a dehydrating agent or solvent to form a compound of general formula (2a).

In another aspect the invention relates to a method wherein a compound of general formula (5a)

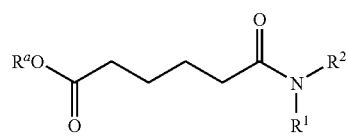

(5a)

is intramolecularly cyclised under basic conditions in the presence of a solvent to form a compound of general formula (3a), wherein
R$^1$, R$^2$ and R$^a$ are as herein before defined.

In another aspect the invention relates to a method wherein a compound of general formula (1a) is reacted in the presence of palladium or palladium(II)-hydroxide on charcoal as catalyst and a solvent under hydrogen pressure to form a compound of general formula (6a)

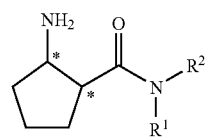

(6a)

In another aspect the invention relates to a method wherein a compound of general formula (2b)

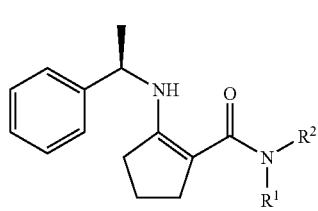

(2b)

is hydrogenated in the presence of a catalyst and a solvent under hydrogen pressure to form a compound of general formula (1b)

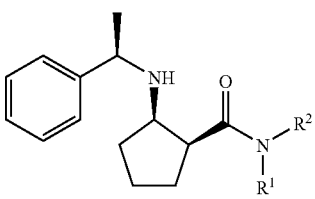

In another aspect the invention relates to a method wherein a compound of general formula (2c)

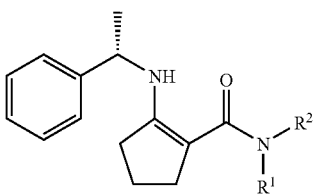

is hydrogenated in the presence of a catalyst and a solvent under hydrogen pressure to form a compound of general formula (1c)

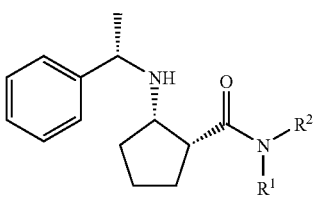

In another aspect the invention relates to compounds selected from among general formulae (2a), (1b) and (1c)

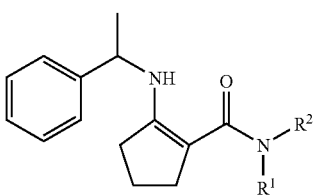

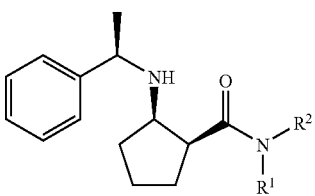

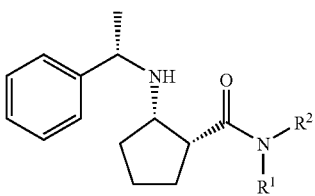

wherein $R^1$ and $R^2$ are as herein before defined.

Definitions

As used herein, the following definitions apply, unless stated otherwise.

By alkyl are meant in each case saturated straight-chain (unbranched) or branched aliphatic hydrocarbon groups (alkyl group). By the groups defined herein before are meant for example methyl, ethyl, propyl, butyl, pentyl, hexyl, heptyl, octyl, nonyl and decyl, these terms encompassing all the possible isomeric forms, such as for example n- and iso-propyl for propyl, n-butyl, iso-butyl, sec.-butyl and tert.-butyl for butyl, etc.

Heteroalkyl represents straight-chain (unbranched) or branched aliphatic hydrocarbon chains, which are interrupted by 1 to 3 heteroatoms, while each of the available carbon and nitrogen atoms in the heteroalkyl chain may optionally be substituted independently of one another and the heteroatoms are each independently selected from among O, N and S (e.g. dimethylaminomethyl, dimethylaminoethyl, dimethylaminopropyl, diethylaminomethyl, diethylaminoethyl, diethylaminopropyl, 2-diisopropylaminoethyl, bis-2-methoxyethylamino, [2-(dimethylamino-ethyl)-ethyl-amino]-methyl, 3-[2-(dimethylamino-ethyl)-ethyl-amino]-propyl, hydroxymethyl, 2-hydroxyethyl, 3-hydroxypropyl, methoxy, ethoxy, propoxy, methoxymethyl, 2-methoxyethyl).

Haloalkyl relates to alkyl as herein before defined, in which one or more hydrogen atoms are replaced by halogen atoms such as for example —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —$CHFCH_2CH_3$ and —$CHFCH_2CF_3$.

Halogen refers to fluorine, chlorine, bromine and/or iodine atoms.

By cycloalkyl are meant mono-, bicyclic or bridged bicyclic rings and spiro systems, while the ring system may be a saturated ring or, however, also an unsaturated, non-aromatic ring, which may optionally also contain double bonds, such as for example cyclopropyl, cyclobutyl, cyclopentyl, cyclohexyl, norbornyl, spiro[2.5]octane and spiro[3.3]heptane.

Cycloalkylalkyl includes a non-cyclic alkyl as herein before defined wherein a hydrogen atom bound to a carbon atom, usually to a terminal C atom, is replaced by a cycloalkyl group as herein before defined.

Aryl relates to monocyclic or bicyclic rings with at least one aromatic ring and 6-12 carbon atoms such as for example phenyl, naphthyl, indanyl and 1,2,3,4-tetrahydronaphthyl.

Arylalkyl includes a non-cyclic alkyl as herein before defined wherein a hydrogen atom bound to a carbon atom, usually to a terminal C atom, is replaced by an aryl group as herein before defined.

By heteroaryl are meant mono- or bi having at least one aromatic ring which contain, instead of one or more carbon atoms, one or more heteroatoms, which may be identical or different, such as e.g. nitrogen, sulphur or oxygen atoms. Examples include furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl and triazinyl. Examples of bicyclic heteroaryl groups are indolyl, isoindolyl, benzofuryl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl, benzotriazinyl, indolizinyl, oxazolopyridyl, imidazopyridyl, naphthyridinyl, indolinyl, isochromanyl, chromanyl, tetrahydroisoquinolinyl, isoindolinyl, isobenzotetrahydrofuryl, isobenzotetrahydrothienyl, isobenzothienyl, benzoxazolyl, pyridopyridyl, benzotetrahydrofuryl, benzotetrahydrothienyl, purinyl, benzodioxolyl, triazinyl, phenoxazinyl, phenothiazinyl, pteridinyl, benzothiazolyl, imidazopyridyl, imidazothiazolyl, dihydrobenzisoxazinyl, benzisoxazinyl, benzoxazinyl, dihydrobenzisothiazinyl, benzopyranyl, benzothiopyranyl, cumarinyl, isocumarinyl, chromonyl, chromanonyl, pyridyl-N-oxide tetrahydroquinolinyl, dihydroquinolinyl, dihydroquinolinonyl, dihydroisoquinolinonyl, dihydrocumarinyl, dihydroisocumarinyl, isoindolinonyl, benzodioxanyl, benzoxazolinonyl, pyrrolyl-N-oxide, pyrimidinyl-N-oxide, pyridazinyl-N-oxide, pyrazinyl-N-oxide, quinolinyl-N-oxide, indolyl-N-oxide, indolinyl-N-oxide, isoquinolyl-N-oxide, quinazolinyl-N-oxide, quinoxalinyl-N-oxide, phthalazinyl-N-oxide, imidazolyl-N-oxide, isoxazolyl-N-oxide, oxazolyl-N-oxide, thiazolyl-N-oxide, indolizinyl-N-oxide, indazolyl-N-oxide, benzothiazolyl-N-oxide, benzimidazolyl-N-oxide, pyrrolyl-N-oxide, oxadiazolyl-N-oxide, thiadiazolyl-N-oxide, triazolyl-N-oxide, tetrazolyl-N-oxide, benzothiopyranyl-S-oxide and benzothiopyranyl-S,S-dioxide.

Heteroarylalkyl encompasses a non-cyclic alkyl as herein before defined wherein a hydrogen atom bound to a carbon atom, usually to a terminal C atom, is replaced by a heteroaryl group as herein before defined.

Heterocycloalkyl relates to saturated or unsaturated, non-aromatic mono-, bicyclic or bridged bicyclic rings and spiro systems having 3-14 carbon atoms, which carry heteroatoms, such as nitrogen, oxygen or sulphur, instead of one or more carbon atoms. Examples of such heterocycloalkyl groups are tetrahydrofuryl, pyrrolidinyl, pyrrolinyl, imidazolidinyl, imidazolinyl, pyrazolidinyl, pyrazolinyl, piperidinyl, piperazinyl, indolinyl, isoindolinyl, morpholinyl, thiomorpholinyl, homomorpholinyl, homopiperidinyl, homopiperazinyl, homothiomorpholinyl, thiomorpholinyl-S-oxide, thiomorpholinyl-S,S-dioxide, tetrahydropyranyl, tetrahydrothienyl, homothiomorpholinyl-S,S-dioxide, oxazolidinonyl, dihydropyrazolyl, dihydropyrrolyl, dihydropyrazinyl, dihydropyridyl, dihydropyrimidinyl, dihydrofuryl, dihydropyranyl, tetrahydrothienyl-S-oxide, tetrahydrothienyl-S,S-dioxide, homothiomorpholinyl-S-oxide, 2-oxa-5-azabicyclo[2.2.1]heptane, 8-oxa-3-aza-bicyclo[3.2.1]octane, 3,8-diaza-bicyclo[3.2.1]octane, 2.5-diaza-bicyclo[2.2.1]heptane, 3,8-diaza-bicyclo[3.2.1]octane, 3.9-diaza-bicyclo[4.2.1]nonane, 2,6-diaza-bicyclo[3.2.2]nonane, 1,4-dioxa-spiro[4.5]decane, 1-oxa-3,8-diaza-spiro[4.5]decane and 2,6-diaza-spiro[3.3]heptane.

Heterocycloalkylalkyl relates to non-cyclic alkyl as herein before defined, wherein a hydrogen atom bound to a carbon atom, usually to a terminal C atom, is replaced by a heterocycloalkyl group as herein before defined.

The use of the symbol "*" indicates that there is a stereogenic centre in the part of the molecule thus marked.

Features and advantages of the present invention will become apparent from the detailed examples that follow, which illustrate the broad outlines of the invention by way of example, without restricting its scope:

EXPERIMENTAL SECTION

Preparation of Cyclic β-ketocarboxamides

Scheme A-1 (when using primary amines the products 3 obtained correspond to the products 7 from Scheme A-2)

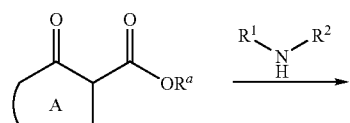

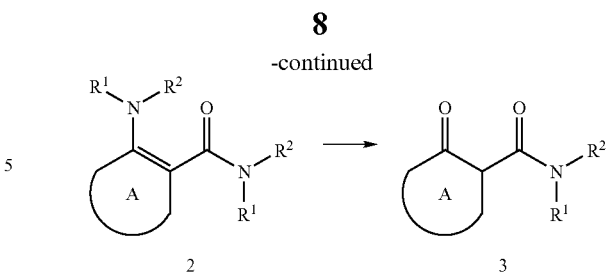

Scheme A-2

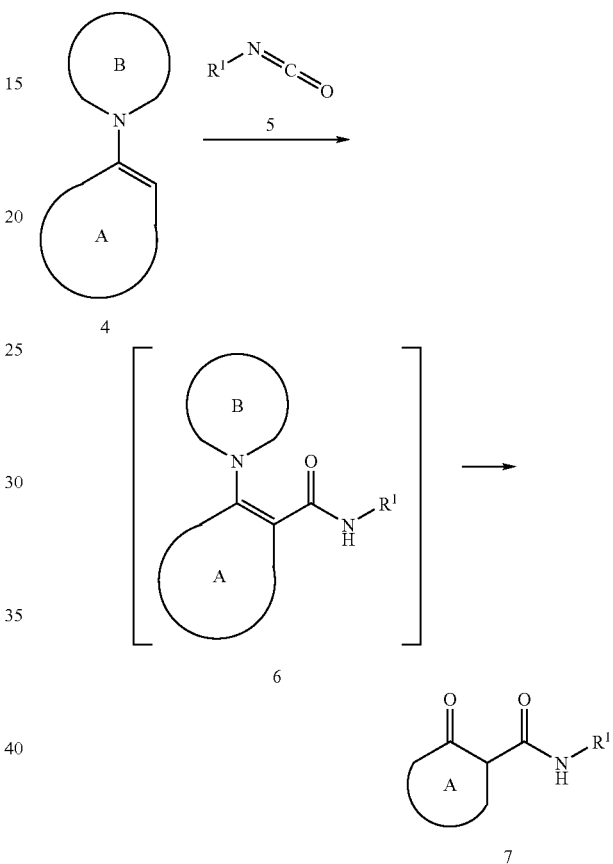

Scheme A-3

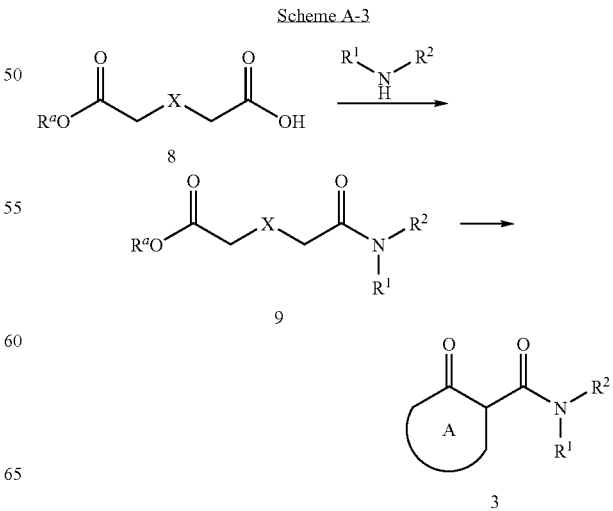

wherein

X corresponds to a 1-7 membered alkylene bridge, in which a methylene group may be replaced by a heteroatom or a group of heteroatoms —O—, —NR$^c$— or —S(O)$_n$—, and R$^a$, R$^c$ and n have the meanings given for formula (1).

Cyclic β-ketocarboxamides of the general structure 3 may be prepared from cyclic β-ketocarboxylates 1 by reacting with primary or secondary amines (Scheme A-1).

Alternatively cyclic β-ketocarboxamides may be prepared starting from nucleophilic cyclic enamines 4 (formally obtainable from cyclic ketones and a cyclic secondary amine B, e.g. morpholine, pyrrolidine) by reacting with suitable isocyanates 5 and subsequent hydrolysis of the intermediate 6 (7, Scheme A-2).

Another way of obtaining cyclic β-ketocarboxamides 3 is through amide formation on a hemiester of a dicarboxylic acid 8 to form the intermediate product 9 which is cyclised in an intramolecular Dieckmann condensation (Scheme A-3).

General Preparation of Chiral Cyclic β-aminocarboxamides

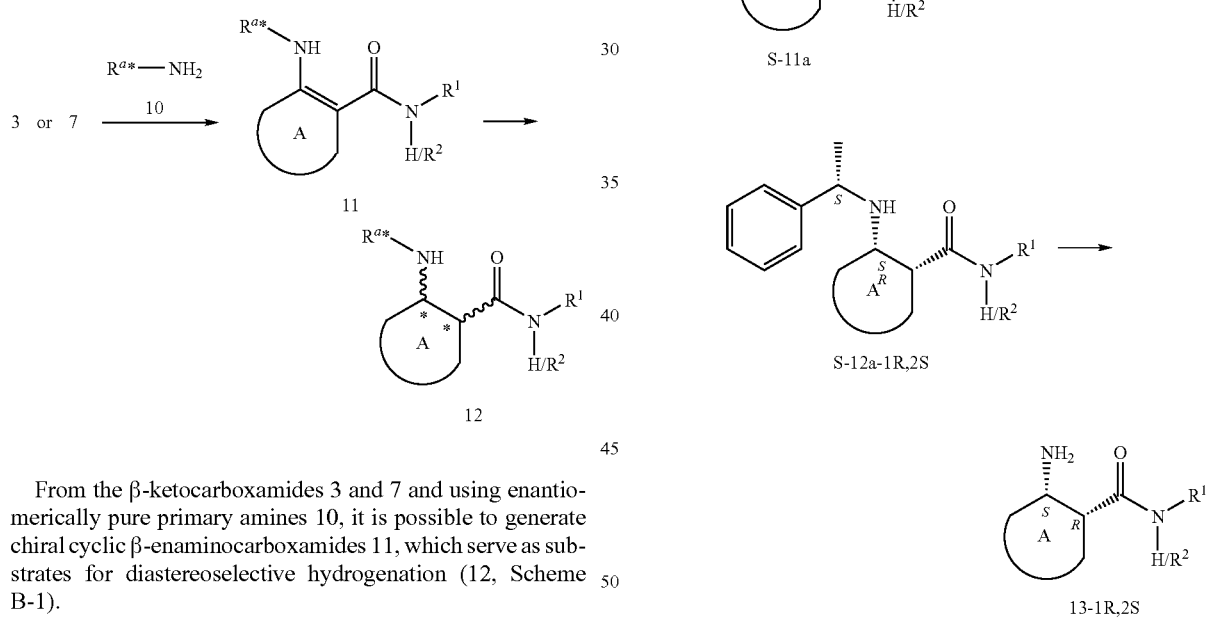

From the β-ketocarboxamides 3 and 7 and using enantiomerically pure primary amines 10, it is possible to generate chiral cyclic β-enaminocarboxamides 11, which serve as substrates for diastereoselective hydrogenation (12, Scheme B-1).

Scheme B-2

Preparation of chiral cyclic β-aminocarboxamides using (R)- or (S)-1-phenylethylamine as chiral auxiliary and the subsequent cleaving thereof to obtain the free amino group.

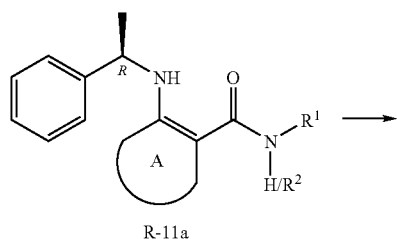

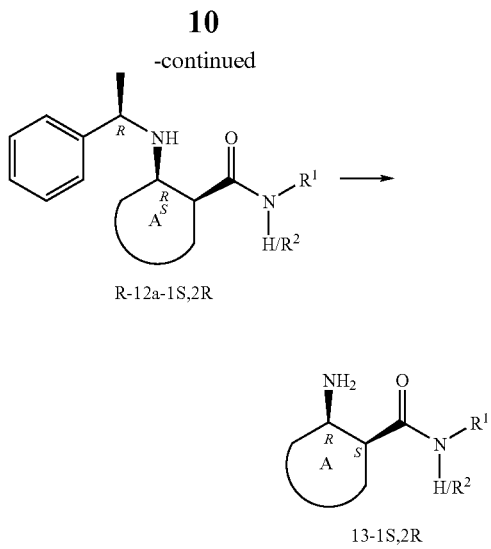

Preferably, chiral primary amines, particularly (R)- or (S)-1-phenylethylamines are used (R-11a or S-11a, Scheme B-2) to form the β-enaminocarboxamides 11. In this way a diastereomer of high selectivity is preferably formed during hydrogenation under the conditions specified below. Preferably a diastereomeric ratio >60:40, particularly >80:20, most particularly preferably >90:10 is thus obtained.

With reference to structurally similar carboxylates of the compounds R-11a and S-11a it is known from the prior art that they can be diastereoselectively hydrogenated by the addition of an excess of acid (in relation to the substrate of the hydrogenation), e.g. acetic acid. However, the application of these reaction conditions to the above substrates 11a leads to overhydrogenation, i.e. the absorption of hydrogen does not stop after one equivalent of H2 has been taken up. The phenyl group of the chiral auxiliary is also hydrogenated. This hydrogenation of phenyl groups is prevented in the method according to the invention by omitting the addition of acid during the hydrogenation of the corresponding β-enaminocarboxamides 11a in the process according to the invention.

After the diastereoselective reduction the desired diastereomer preferably formed may be purified by direct crystallisation from a lipophilic solvent such as for example methylcyclohexane or from polar solvent mixtures such as for example alcohol/water, i.e. the intermediate products R-12a-1S,2R or S-12a-1R,2S do not have to be precipitated in the form of a salt and have diastereomeric purities of >99%.

When using (R)-1-phenylethylamine as chiral auxiliary the two newly generated stereogenic centres in R-12a predominantly have the configuration 1S,2R, and when (S)-1-phenylethylamine is used in S-12a the configuration is accordingly 1R,2S, i.e. in each case there is a cis configuration at the ring A (R-12a-1S,2R or S-12a-1R,2S, Scheme B-2). By subsequent hydrogenolytic cleaving of the phenethyl group the corresponding cyclic β-aminocarboxamides 13-1S,2R or 13-1R,2S are obtained in enantiomeric purities of >99%.

Suitable solvents used may be both protic and aprotic solvents. Protic solvents include for example water and alcohols, such as e.g. methanol, ethanol, 1-propanol, 2-propanol, 1-butanol, 2-butanol, ethyleneglycol and trifluorethanol. The aprotic solvents include inter alia ethers, for example tetrahydrofuran (THF), 2-methyltetrahydrofuran, 1,4-dioxane and dimethoxyethane, carboxamides, such as e.g. dimethylformamide and dimethylacetamide, N-methylpyrrolidinone, N-ethylpyrrolidinone, dimethylsulphoxide, sulpholane, dimethylpropylurea, acetonitrile, esters of acetic acid, such as e.g. ethyl acetate and isopropyl acetate, ketones, such as acetone, ethylmethylketone and methylisobutylketone, hydrocarbons, such as toluene or methylcyclohexane and mixtures of the above-mentioned solvents.

Dehydrating agents used may be orthoesters such as e.g. trimethyl orthoformate or metal compounds such as e.g. titanium tetraisopropoxide.

Suitable hydrogenation catalysts include in particular transition metals such as e.g. palladium, nickel, rhodium, ruthenium and iridium. The metals may also be dispersed on a carrier material. Particularly suitable catalysts are platinum, for example platinum on activated charcoal or also platinum (IV)-dioxide, Raney nickel or palladium, such as for example palladium on activated charcoal.

The hydrogen pressure is in the range from 1-150 bar, preferably in the range from 1-100 bar and particularly preferably in the range from 1-80 bar.

The temperature during hydrogenation is in the range from 0-150° C., preferably in the range from 10-100° C. and particularly preferably in the range from 20-80° C.

The amount of hydrogenation catalyst used, based on the hydrogenation substrate, is in the range from 0.01-50 wt. %, preferably in the range from 0.05-30 wt. %, and particularly preferably in the range from 0.1-20 wt. %.

The use of the method according to the invention for preparing cyclic β-aminocarboxamides is hereinafter described by way of example, the substituents of the general formulae having the meanings specified herein before. These synthesis examples are intended to illustrate the invention without restricting it to their content and without restricting the scope of the method features to these Examples. Where the preparation of starting compounds has not been described they are commercially available or may be prepared analogously to known compounds or methods described here. Substances described in the literature are prepared according to the published methods of synthesis.

Example 1

Preparation of the β-ketocarboxamide 7-a (Method of Synthesis 1)

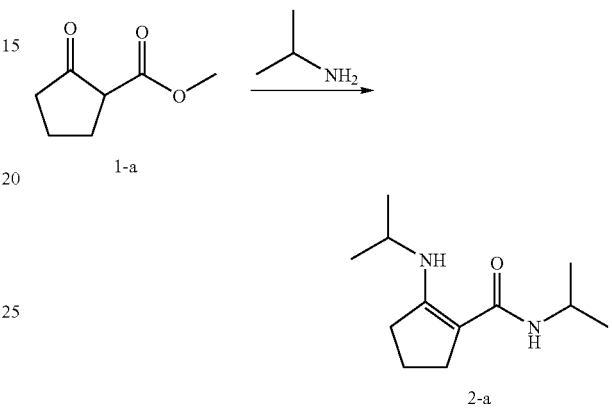

Methyl cyclopentanone-2-carboxylate 1-a (400 g) and isopropylamine (860 g) are heated to 160° C. in cyclohexane (4 L) in a pressurised reactor for 3 hours (h). The solvent is evaporated down. Methylcyclohexane (500 mL) is added to the residue and it is heated to 60-70° C. The reaction mixture is stirred for 16 h at room temperature (RT) and after cooling stirred for a further 2 h at −10° C. The solid is suction filtered and washed with cold methylcyclohexane. 225 g amide 2-a are obtained.

MS-ESI$^+$: 211 (M+H)$^+$

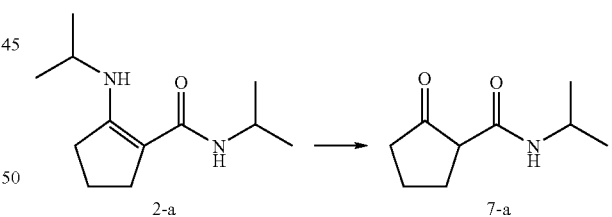

A solution of amide 2-a (222 g) in tetrahydrofuran (700 mL) is combined with 6 N hydrochloric acid (270 mL) and stirred for 16 h at RT and 11 h at 40-50° C. After the addition of concentrated hydrochloric acid (74 g) the mixture is stirred for another 16 h at RT, saturated saline solution (500 mL) is added and the salts precipitated are suction filtered. The organic phase is separated off, washed with saturated saline solution (250 mL), dried on sodium sulphate and evaporated down several times with toluene. The solid remaining is digested with ethyl acetate (700 mL), the suspension formed is suction filtered and the filtrate is evaporated down. 155 g β-ketocarboxamide 7-a are obtained.

MS-ESI$^+$: 170 (M+H)$^+$

Example 2

Preparation of β-ketocarboxamide 7-a (Method of Synthesis 2)

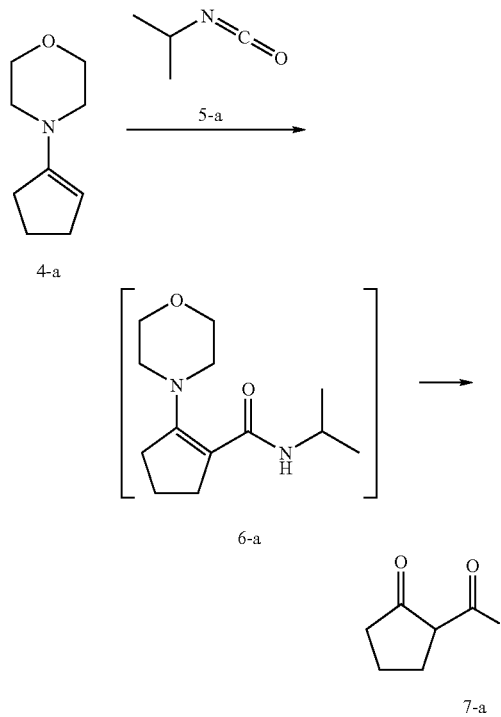

A solution of N-(1-cyclopenten-1-yl)morpholine 4-a (144 mL) and isopropylisocyanate 5-a (86.4 mL) in toluene (300 mL) is stirred for 2 h at 70° C. After cooling to 20° C., 6 N hydrochloric acid (250 mL) is added with vigorous stirring and thorough cooling. The mixture is stirred for 1.5 h at 20° C., the precipitated solid is suction filtered and washed with toluene (100 mL). The toluene phase is separated off, the aqueous phase is extracted several times with methylene chloride (in each case 100 mL). The organic phases are combined, dried on sodium sulphate and evaporated down (crude product A). The solid suction filtered is digested 3 times with methylene chloride (in each case 100 mL), the combined methylene chloride phases are dried and the solvent is evaporated down (crude product B).

The combined crude products A and B are distilled under reduced pressure. 102 g β-ketocarboxamide 7-a are obtained. (B.p.: 150° C. at 0.1 mbar)

MS-ESI⁺: 170 (M+H)⁺

Example 3a

Preparation of β-ketocarboxamide 7-a (Method of Synthesis 3)

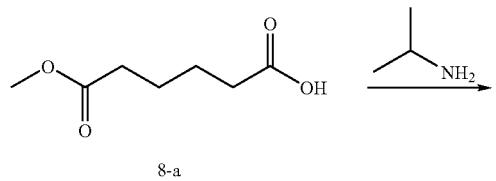

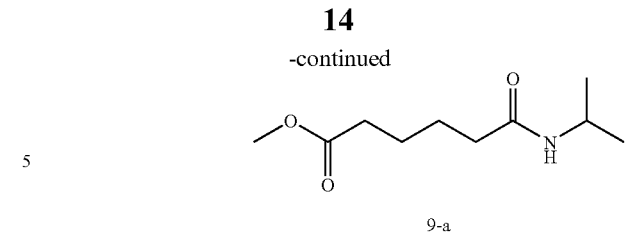

Monomethyl adipate 8-a (2.56 kg) in toluene (21.5 L) and dimethylformamide (30 mL) are refluxed. Within 0.5 h thionyl chloride (1.22 L) is added dropwise (large amounts of gas given off). The mixture is refluxed for a further 1.6 h and then toluene (13 L) is distilled off under slightly reduced pressure. After cooling to 20° C. toluene (10 L) is added, the mixture is cooled to 6° C. and a solution of 2-propylamine (2.83 kg) in toluene (3 L) is added, so that the temperature does not exceed 13° C. It is stirred for 16 h at RT and the precipitated 2-propylamine hydrochloride is filtered off. The filtrate is combined with activated charcoal (600 g), filtered and the solvent is evaporated down. 4.2 kg of an oil are obtained which solidifies on cooling. The crude product (9-a) contains residual amounts of toluene and is used in the next step without any further purification.

MS-ESI⁺: 202 (M+H)⁺

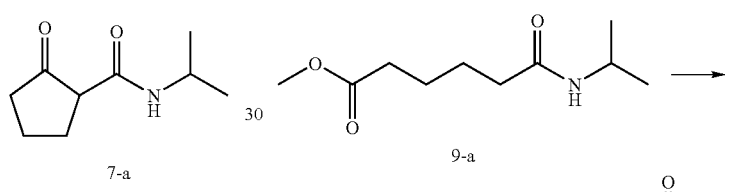

Potassium-tert.-butoxide (1.07 kg) in toluene (20 L) is refluxed. A solution of the crude product 9-a (1.61 kg) in toluene (10 L) is added to this solution, the mixture is refluxed for 2 h and in this time toluene (6 L) is distilled off. Toluene (3 L) is added and distilled off again (4 L). After cooling to 17° C. 6 N hydrochloric acid (1.67 L) is added and the precipitated potassium chloride is filtered through a suction filter lined with activated charcoal. The filtrate is evaporated down and the residue is crystallised from ethyl acetate/methylcyclohexane. 774 g β-ketocarboxamide 7-a are obtained. Another 252 g β-ketocarboxamide 7-a can be isolated from the activated charcoal filter residue by extraction with tetrahydrofuran.

MS-ESI⁺: 170 (M+H)⁺

Example 3b

Preparation of the β-ketocarboxamide 7-a (Method of Synthesis 3)

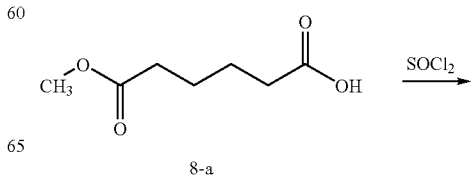

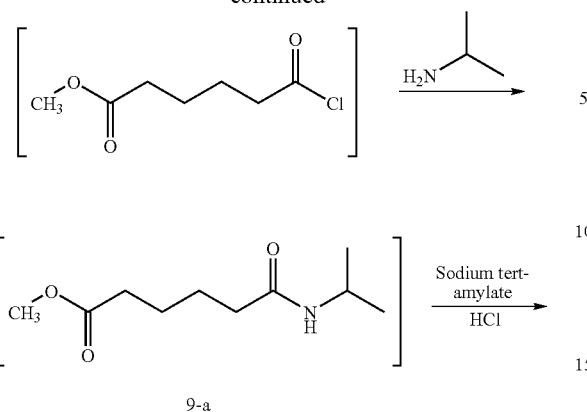

9-a

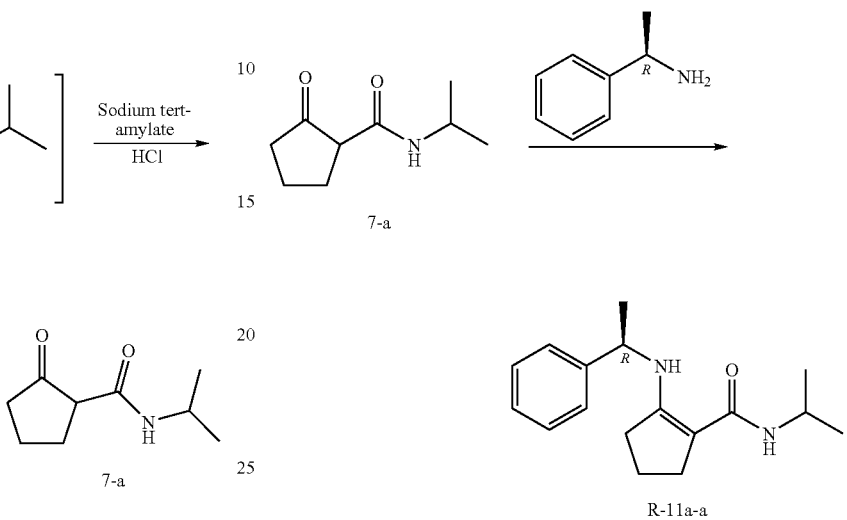

7-a i) Preparation of Acid Chloride

Monomethyl adipate 8-a (20 kg) in toluene (180 L) and dimethylformamide (300 mL) are heated to 70° C. Thionyl chloride (16.34 kg) is metered in within 1 h. The mixture is rinsed with toluene (10 L) and the reaction mixture is stirred for 1 h at 70° C. Then toluene (50 L) is distilled off under reduced pressure.

ii) Amide Formation

The acid chloride solution is cooled to 15° C. At 15 to 25° C. a solution of isopropylamine (18.45 kg) in toluene (30 L) is metered in. It is rinsed with toluene (10 L) and the reaction mixture is stirred for 30 min at 20° C. It is heated to 40° C. and demineralised water (18 L) is added. The aqueous phase is separated off. 60 L solvent are distilled off from the organic phase under reduced pressure.

iii) Cyclisation

Sodium-tert.-amylate (66.02 kg, 25% in toluene) in toluene (80 L) and tert.-amylalcohol (80 L) are heated to 100° C. The amide solution is added to this solution at 100° C. within 1 h. It is rinsed with toluene (20 L) and the suspension is stirred for 1-2 h at 95-100° C. It is cooled to 30°-40° C. and diluted with demineralised water (30 L). At 30 to 40° C. hydrochloric acid (18.97 kg, 30%, industrial grade) is added and the mixture is rinsed with demineralised water (6 L). The aqueous phase is separated off. 282 L solvent are distilled off from the organic phase under reduced pressure.

The product solution is heated to 50° C. and at 40-50° C. diluted with methylcyclohexane (160 L). Within 2 h the mixture is cooled to 4° C. and stirred for another 30 min at this temperature. The product is centrifuged off and washed with a mixture of methylcyclohexane (20 L) and toluene (20 L). The product is dried at 40° C. 15.4 kg product 7-a are obtained.

Example 4a

Preparation of the Cyclic β-enaminocarboxamide R-11a-a

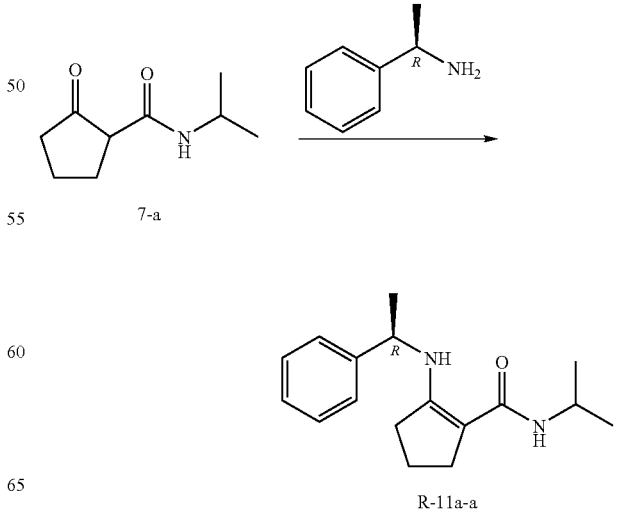

A solution of β-ketocarboxamide 7-a (11.3 g) and (R)-1-phenylethylamine (9 g) in toluene is evaporated down at 60-70° C. under reduced pressure using the rotary evaporator. Toluene is added until no more water goes over azeotropically. The solvent is then evaporated down completely. The residue is combined with methylcyclohexane (150 mL) and heated to 70° C. After cooling the mixture is stirred for 2 h at 0° C., the solid is suction filtered and washed with cold methylcyclohexane. 13.5 g β-enaminocarboxamide R-11a-a are obtained.

MS-ESI⁺: 273 (M+H)⁺

Example 4b

Preparation of the Cyclic β-enaminocarboxamide R-11a-a

β-Ketocarboxamide 7-a (15 kg) in toluene (105 L) is heated to 105° C. At this temperature (R)-1-phenylethylamine (11.82 kg) is added and the mixture is rinsed with 15 L toluene. It is refluxed using the water separator until no more water separates off. The mixture is cooled to 30° C. and demineralised water (15 L) is added. The aqueous phase is separated off. Under reduced pressure 105 L toluene are distilled off from the organic phase. Then methylcyclohexane (75 L) is added at 50° C. and 30 L solvent are again distilled off under reduced pressure. 7.5 L tert.-butylmethylether are added to the residue at 55° C. and the mixture is cooled to 43° C. It is inoculated and cooled to 15° C. within 1 h. After 30 min stirring at 15° C. the product is centrifuged off, washed with methylcyclohexane (30 L) and dried at 40° C. in the drying cupboard. 17.3 kg product R-11a-a are obtained.

Example 5a

Preparation of the Cyclic β-aminocarboxamide R-12a-a-1S,2R

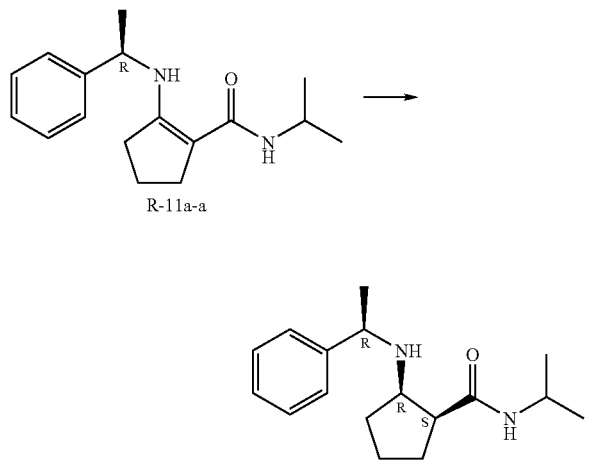

A solution of the β-enaminocarboxamide R-11a-a (108 g) in absolute ethanol (1 L) is hydrogenated for 3 h in the presence of platinum(IV)-dioxide (6 g) at 20° C. under a hydrogen pressure of 5 bar. The catalyst is filtered off and the solution is evaporated down. The crude product obtained (1S,2R:1R,2S=94:6, HPLC) is dissolved in methylcyclohexane (500 mL), filtered clear, cooled to −19° C., the precipitate is suction filtered and the filter cake is washed with cold methylcyclohexane. 80 g β-aminocarboxamide R-12a-a-1S, 2R are obtained. (1S,2R:1R,2S>99:1, HPLC)

MS-ESI$^+$: 275 (M+H)$^+$

Analogously to the process described above, the hydrogenation of the β-enaminocarboxamide R-11a-a is carried out in methanol in the presence of platinum(IV)-dioxide at 30° C. under a hydrogen pressure of 20 bar until the uptake of hydrogen stops.

Example 5b

Preparation of the Cyclic β-aminocarboxamide R-12a-a-1S,2R

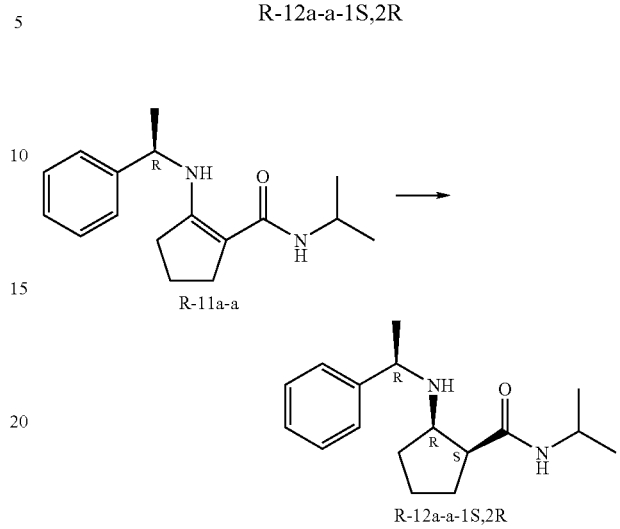

A solution of the β-enaminocarboxamide R-11a-a (50 g) in methanol (250 mL) is hydrogenated in the presence of platinum(IV)-dioxide (0.5 g) and activated charcoal (5 g) at 20° C. under a hydrogen pressure of 60 psi. The reaction is monitored using thin layer chromatography. After the reaction has ended the catalyst is filtered off and washed with 50 mL methanol (diastereoselectivity: 1S,2R:1R,2S=96:4, HPLC). 200 mL of methanol are distilled off and 250 mL of n-heptane are added. 150 mL solvent are distilled off azeotropically. Another 200 mL n-heptane are added and again 100 mL of solvent are distilled off azeotropically. The mixture is cooled to 45° C. and inoculated. It is cooled to 20° C. and stirred for 30 min at this temperature. The mixture is suction filtered and washed with n-heptane. 37.5 g β-aminocarboxamide R-12a-a-1S,2R (1S,2R:1R,2S>99.5:0.5, HPLC) are obtained.

Example 6a

Preparation of the Cyclic Free β-aminocarboxamide 13-a-1S,2R [cispentacin-isopropylamide, (1S,2R)-2-amino-1-cyclopentanecarboxylic acid isopropylamide]

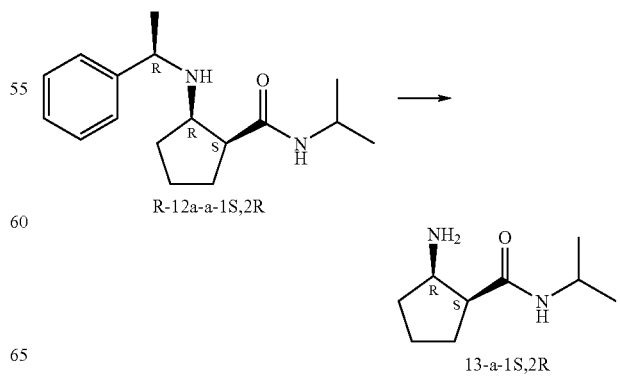

A solution of the β-aminocarboxamide R-12a-a-1S,2R (82.5 g) in methanol (700 mL) is hydrogenated for 6 h in the presence of palladium(II)-hydroxide on activated charcoal (8 g, 20 wt. %) at 50° C. under a hydrogen pressure of 4 bar. The catalyst is filtered off and the solution is evaporated down. (1S,2R)-2-amino-1-cyclopentanecarboxylic acid-isopropylamide 13-a-1S,2R is obtained as an oil, which crystallises out (1S,2R:1R,2S>99:1, chiral HPLC).

MS-ESI+: 171 (M+H)+

Analogously to the preparation of (1S,2R)-2-amino-1-cyclopentanecarboxylic acid isopropylamide 13-a-1S,2R the corresponding (1R,2S)-2-amino-1-cyclopentanecarboxylic acid-isopropylamide 13-a-1R,2S is prepared using (S)-1-phenylethylamine.

MS-ESI+: 171 (M+H)+

Example 6b

Preparation of the Cyclic Free β-aminocarboxamide 13-a-1S,2R [cispentacin-isopropylamide, (1S,2R)-2-amino-1-cyclopentanecarboxylic acid isopropylamide]

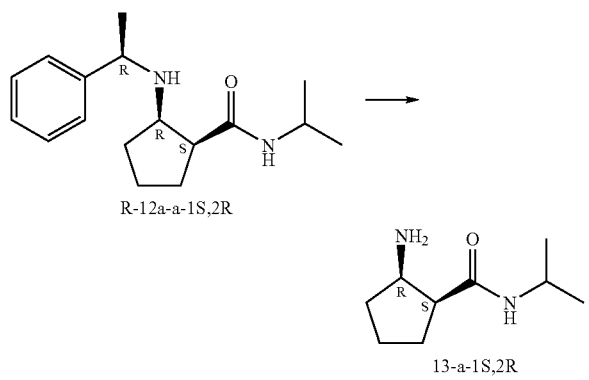

A solution of the β-aminocarboxamide R-12a-a-1S,2R (30 g) in methanol (300 mL) is hydrogenated in the presence of palladium on activated charcoal (3 g, 10 wt. %) at 40° C. under a hydrogen pressure of 60 psi. The catalyst is filtered off and the solution is evaporated down. 18.2 g (1S,2R)-2-amino-1-cyclopentanecarboxylic acid isopropylamide 13-a-1S,2R is obtained as an oil that crystallises out (1S,2R:1R,2S>99:1, chiral HPLC).

General Preparation of Salts

The salts of compounds according to the invention are prepared by dissolving the compound in a suitable solvent, such as e.g. an acetic acid ester, or in a suitable mixture of solvents, such as e.g. an alcohol and a lipophilic solvent, such as e.g. methylcylohexane or toluene, and adding a solution of an organic or inorganic acid in a suitable solvent or mixture of solvents or by directly adding an organic or inorganic acid. The crystalline salts formed are filtered off or centrifuged and dried.

Example 7a

Preparation of the Hydrochloride 9.5 g 13-a-1S,2R are dissolved in 120 mL ethyl acetate. At a temperature of 40-50° C. 5.58 mL of a 10 molar solution of hydrogen chloride in ethanol is added. The suspension is stirred for 30 min at 50° C., cooled to 20° C. and suction filtered. It is washed with 20 mL ethyl acetate and dried at 40° C. in the circulating air dryer. 9.5 g hydrochloride salt are obtained.

Melting point: 183-184° C.

Example 7b

Preparation of the Benzenesulphonic Acid Salt 4.9 g 13-a-1S,2R are dissolved in 10 mL ethanol and 40 mL methylcyclohexane. 4.55 g benzenesulphonic acid are added. The suspension formed is stirred for 1.5 h and suction filtered. It is washed with 10 mL methylcyclohexane and dried at 40° C. in the circulating air dryer. 8.05 g benzenesulphonic acid salt are obtained.

Melting point: 152-153° C.

Example 7c

The p-toluenesulphonic acid salt is prepared analogously to Example 7b.

Melting point: 155-156° C.

The invention claimed is:

1. A method of preparing a compound of formula (1a),

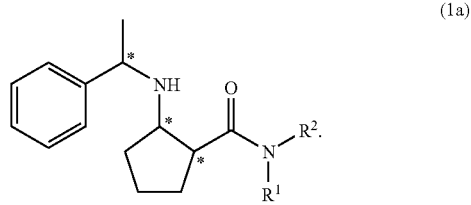

(1a)

wherein $R^1$ and $R^2$ each independently denote hydrogen or a group selected from among $C_{1-8}$alkyl, $C_{3-8}$cycloalkyl, $C_{4-12}$cycloalkylalkyl, 5-6 membered heteroaryl and 3-8 membered heterocycloalkyl, optionally substituted by one or more identical or different $R^a$ and/or $R^b$, or $R^1$ and $R^2$ together with the nitrogen atom to which they are bound form a 3-14 membered heterocycloalkyl or 5-12 membered heteroaryl, this ring system optionally being substituted by one or more identical or different $R^a$ and/or $R^b$, and each $R^a$ is independently selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-8 membered heterocycloalkyl and 4-14 membered heterocycloalkylalkyl, and each $R^b$ is independently selected from among —$OR^c$, $C_{1-3}$haloalkyloxy, —$OCF_3$, —$SR^c$, —$NR^cR^c$, —$ONR^c R^c$, —$N(OR^c)R^c$, —$N(R^c)NR^cR^c$, halogen, —$CF_3$, —CN, —NC, —OCN, —SCN, —NO, —$NO_2$, —$N_3$, —$S(O)R^c$, —$S(O)OR^c$, —$S(O)_2R^c$, —$S(O)_2OR^c$, —$S(O)NR^cR^c$, —$S(O)_2NR^cR^c$, —$OS(O)R^c$, —$OS(O)_2R^c$, —$OS(O)_2OR^c$, —$OS(O)NR^cR^c$, —$OS(O)_2NR^cR^c$, —$C(O)R^c$, —$C(O)OR^c$, —$C(O)SR^c$, —$C(O)NR^cR^c$, —$C(O)N(R^c)NR^cR^c$, —$C(O)N(R^c)OR^c$, —$C(NR^c)NR^cR^c$, —$C(NOH)R^c$, —$C(NOH)NR^cR^c$, —$OC(O)R^c$, —$OC(O)OR^c$, —$OC(O)SR^c$, —$OC(O)NR^cR^c$, —$OC(NR^c)NR^cR^c$, —$SC(O)R^c$, —$SC(O)OR^c$, —$SC(O)NR^cR^c$, —$SC(NR^c)NR^cR^c$, —$N(R^c)C(O)R^c$, —N[C(O)

$R^c]_2$, —N(OR$^c$)C(O)R$^c$, —N(R$^c$)C(NR$^c$)R$^c$, —N(R$^c$)N(R$^c$)C(O)R$^c$, —N[C(O)R$^c$]NR$^c$R$^c$, —N(R$^c$)C(S)R$^c$, —N(R$^c$)S(O)R$^c$, —N(R$^c$)S(O)OR$^c$, —N(R$^c$)S(O)$_2$R$^c$, —N[S(O)$_2$R$^c$]$_2$, —N(R$^c$)S(O)$_2$OR$^c$, —N(R$^c$)S(O)$_2$NR$^c$R$^c$, —N(R$^c$)[S(O)$_2$]$_2$R$^c$, —N(R$^c$)C(O)OR$^c$, —N(R$^c$)C(O)SR$^c$, —N(R$^c$)C(O)NR$^c$R$^c$, —N(R$^c$)C(O)NR$^c$NR$^c$R$^c$, —N(R$^c$)N(R$^c$)C(O)NR$^c$R$^c$, —N(R$^c$)C(S)NR$^c$R$^c$, —[N(R$^c$)C(O)]$_2$R$^c$, —N(R$^c$) [C(O)]$_2$R$^c$, —N{[C(O)]$_2$R$^c$}$_2$, —N(R$^c$)[C(O)]$_2$OR$^c$, —N(R$^c$)[C(O)]$_2$NR$^c$R$^c$, —N{[C(O)]$_2$OR$^c$}$_2$, —N{[C(O)]$_2$NR$^c$R$^c$}$_2$, —[N(R$^c$)C(O)]$_2$OR$^c$, —N(R$^c$)C(NR$^c$)OR$^c$, —N(R$^c$)C(NOH)R$^c$, —N(R$^c$)C(NR$^c$)SR$^c$ and —N(R$^c$)C(NR$^c$)NR$^c$R$^c$, and each R$^c$ independently denotes hydrogen or C$_{1-6}$alkyl, comprising hydrogenating a compound of formula (2a)

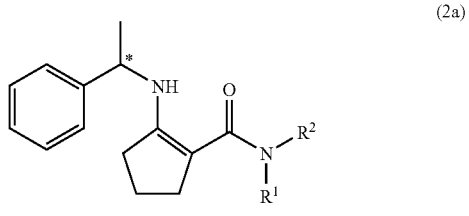

(2a)

wherein R$^1$ and R$^2$ are as defined above in the presence of platinum(IV)-dioxide as catalyst and a solvent under hydrogen pressure, wherein the hydrogenation is carried out without any addition of acids.

2. The method according to claim 1, further comprising the further step of reacting a compound of formula (3a)

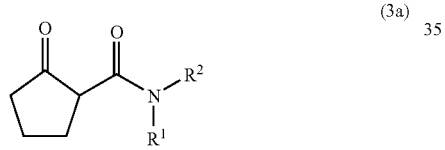

(3a)

with 1-phenylethylamine in the presence of a dehydrating agent or solvent to form a compound of formula (2a), wherein R$^1$ and R$^2$ are as defined in claim 1.

3. The method according to claim 2, further comprising the step of cyclizing intramolecularly a compound of formula (5a)

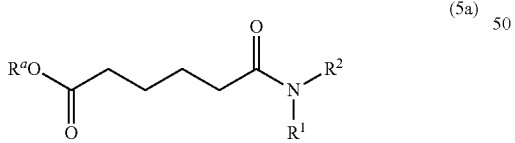

(5a)

under basic conditions in the presence of a solvent to form a compound of formula (3a), wherein R$^1$, R$^2$ and R$^a$ are as defined in claim 1.

4. The method according to claim 1, wherein a compound of formula (2b)

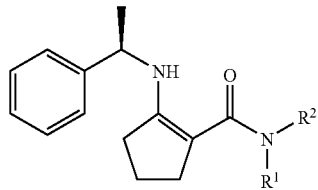

(2b)

is hydrogenated in the presence of a catalyst and a solvent under hydrogen pressure to form a compound of formula (1b)

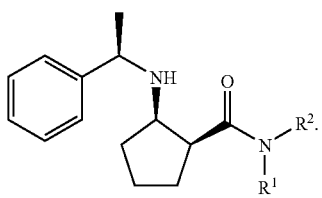

(1b)

wherein R$^1$ and R$^2$ are as defined in claim 1.

5. The method according to claim 1, wherein a compound of formula (2c)

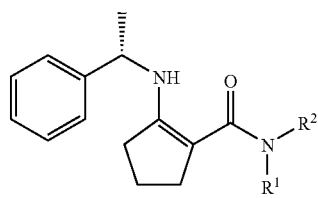

(2c)

is hydrogenated in the presence of platinum(IV)-dioxide and a solvent under hydrogen pressure to form a compound of formula (1c)

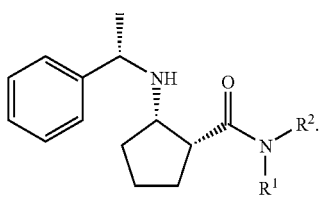

(1c)

wherein R$^1$ and R$^2$ are as defined in claim 1.

6. The method according to claim 1, wherein R$^1$ is hydrogen and R$^2$ is iso-propyl.

* * * * *

UNITED STATES PATENT AND TRADEMARK OFFICE
CERTIFICATE OF CORRECTION

PATENT NO.       : 8,466,318 B2                                    Page 1 of 1
APPLICATION NO.  : 12/301131
DATED            : June 18, 2013
INVENTOR(S)      : Linz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 858 days.

Signed and Sealed this
Eighth Day of September, 2015

Michelle K. Lee
*Director of the United States Patent and Trademark Office*